United States Patent
Perkins et al.

(10) Patent No.: US 9,983,186 B2
(45) Date of Patent: May 29, 2018

(54) OPTICAL COMPUTING DEVICE HAVING TUNABLE DETECTOR WITH NON-PLANAR SEMICONDUCTOR STRUCTURE

(71) Applicant: Halliburton Energy Services, Inc., Houston, TX (US)

(72) Inventors: David L. Perkins, The Woodlands, TX (US); Li Gao, Katy, TX (US); James M. Price, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days. days.

(21) Appl. No.: 15/031,201

(22) PCT Filed: Dec. 18, 2013

(86) PCT No.: PCT/US2013/076249
§ 371 (c)(1),
(2) Date: Apr. 21, 2016

(87) PCT Pub. No.: WO2015/094247
PCT Pub. Date: Jun. 25, 2015

(65) Prior Publication Data
US 2016/0274077 A1    Sep. 22, 2016

(51) Int. Cl.
*G01N 33/28* (2006.01)
*G06E 3/00* (2006.01)
(Continued)

(52) U.S. Cl.
CPC ........ *G01N 33/2823* (2013.01); *G01J 3/0205* (2013.01); *G01J 3/12* (2013.01);
(Continued)

(58) Field of Classification Search
CPC .. G02B 1/043; G02B 2207/109; G02B 21/32; G02B 6/00; G02B 6/0036; G02B 6/0043;
(Continued)

(56) References Cited

U.S. PATENT DOCUMENTS 5,784,507 A    7/1998  Holm-Kennedy et al.
6,383,251 B1 *  5/2002  Sherwood ............. C21B 13/085
                                                    266/182

(Continued)

OTHER PUBLICATIONS

International Search Report and The Written Opinion of the International Search Authority, or the Declaration, dated May 1, 2014, PCT/US2013/076249, 13 pages, ISA/US.

(Continued)

*Primary Examiner* — Michael P Stafira
(74) *Attorney, Agent, or Firm* — Haynes and Boone, LLP (57) ABSTRACT

An optical computing device including a detector having a non-planar semiconductor structure is provided. The detector may include one or more structures having structure characteristics that may be optimized to respond to and weight predetermined wavelengths of light radiated from a sample that are related to characteristics of the sample. The detector may include an array of the one or more structures, wherein each of the structure units may be individually addressable to program or tune the detector to respond to and weight a spectra of light and generate an output signal based on the weighted spectra of light that is proportional to the characteristics of the sample.

16 Claims, 10 Drawing Sheets

(51) Int. Cl.
*G01J 3/02* (2006.01)
*G01J 3/12* (2006.01)
*G01J 3/42* (2006.01)
*G01N 21/31* (2006.01)
*G01N 21/64* (2006.01)
*H01L 31/0352* (2006.01)
*G01J 3/26* (2006.01)

(52) U.S. Cl.
CPC ............. *G01J 3/42* (2013.01); *G01N 21/31* (2013.01); *G01N 21/64* (2013.01); *G06E 3/00* (2013.01); *H01L 31/0352* (2013.01); *G01J 3/26* (2013.01); *G01J 2003/1213* (2013.01); *G01J 2003/1282* (2013.01)

(58) Field of Classification Search
CPC ............. G02B 6/06; G01N 15/1456; G01N 2015/1497; G01N 2015/0693; G01N 2520/00; G01N 33/56916; G01N 15/0227; G01N 15/1434
See application file for complete search history.

(56) References Cited

U.S. PATENT DOCUMENTS

| | | | |
|---|---|---|---|
| 6,388,251 B1 | 5/2002 | Papanyan | |
| 7,015,457 B2 * | 3/2006 | Cole | G01B 11/272 250/226 |
| 7,196,790 B2 * | 3/2007 | Cole | G01B 11/272 250/226 |
| 2003/0206741 A1 * | 11/2003 | Ledentsov | H01S 5/18302 398/79 |
| 2005/0036533 A1 * | 2/2005 | Cox | H01S 5/18386 372/99 |
| 2005/0083533 A1 * | 4/2005 | Atia | G01J 3/10 356/454 |
| 2006/0132782 A1 * | 6/2006 | Flanders | G01J 3/02 356/432 |
| 2006/0139646 A1 * | 6/2006 | DiFoggio | E21B 49/10 356/436 |
| 2009/0236525 A1 * | 9/2009 | Mitra | G01J 3/26 250/338.4 |
| 2010/0182605 A1 * | 7/2010 | Stockwell | G01J 3/12 356/436 |
| 2013/0146773 A1 * | 6/2013 | Ouvrier-Buffet | G01J 5/20 250/349 |

OTHER PUBLICATIONS

K. Balram and D. Miller, "Self-Aligned Silicon Fins in Metallic Slits as a Platform for Planar Wavelength-Selective Nanoscale Resonant Photodetectors," Optics Express, Sep. 24, 2012, vol. 20, No. 20, pp. 22735-22742.

* cited by examiner

| $\lambda_{11}$ | $\lambda_{12}$ | $\lambda_{13}$ | $\lambda_{14}$ | ⋮ | $\lambda_{1M}$ |
|---|---|---|---|---|---|
| $\lambda_{21}$ | $\lambda_{22}$ | $\lambda_{23}$ | $\lambda_{24}$ | ⋮ | $\lambda_{2M}$ |
| $\lambda_{31}$ | $\lambda_{32}$ | $\lambda_{33}$ | $\lambda_{34}$ | ⋮ | $\lambda_{3M}$ |
| ⋯ | ⋯ | ⋯ | ⋯ | ⋯ | ⋯ |
| $\lambda_{N1}$ | $\lambda_{N2}$ | $\lambda_{N3}$ | $\lambda_{N4}$ | ⋮ | $\lambda_{NM}$ |

OPTICAL COMPUTING DEVICE HAVING TUNABLE DETECTOR WITH NON-PLANAR SEMICONDUCTOR STRUCTURE

The present application is a U.S. National Stage patent application of International Patent Application No. PCT/US2013/076249, filed on Dec. 18, 2013, the benefit of which is claimed and the disclosure of which is incorporated herein by reference in its entirety.

TECHNICAL FIELD

Embodiments described herein generally relate to optical systems and, more specifically, to an optical computing device that includes a detector having a non-planar semiconductor structure that can be manufactured to have particular characteristics that may tune the detector to respond to and weight particular wavelengths of incident light.

BACKGROUND

In recent years, optical computing techniques have been developed for applications in the Oil and Gas Industry in the form of optical sensors on downhole or surface equipment to evaluate a variety of fluid properties. An optical computing device may be a device configured to receive an input of electromagnetic radiation from a substance or sample of the substance and produce an output of electromagnetic radiation from a processing element, also referred to as an optical element. The optical element may be, for example, an interference based thin film, or an Integrated Computational Element ("ICE") (also known as a Multivariate Optical Element ("MOE")).

Fundamentally, optical computing devices such as an ICE may utilize optical elements to perform calculations, as opposed to the hardwired circuits of conventional electronic processors. When light from a light source interacts with a substance, unique physical and chemical information about the substance may be encoded in the electromagnetic radiation that is reflected from, transmitted through, or radiated from the sample. Thus, the optical computing device, through use of the optical element and one or more detectors, may be capable of extracting the information of one or multiple characteristics/properties or analytes within the substance and converting that information into a detectable output signal reflecting the overall properties of a sample.

Optical computing devices such as ICEs may use spectrally resolved optical elements to analyze the electromagnetic radiation from a sample. These passive elements may require re-calibration procedures to correct for fabrication errors. Moreover, downhole hydrocarbon wells may have harsh and changing environmental conditions, such as temperature, pressure, and humidity adversely affect the performance and require that the passive elements be re-calibrated. These passive elements may include as many as 50 or more thin dielectric layers prone to contraction or expansion, according to different environmental conditions. Moreover, some ICEs may use multiple passive devices mounted onto a rotating wheel, which may increase device overhead in a limited space environment, such as in a downhole oil exploration and extraction application. Furthermore, rotating passive elements may be difficult to align with flowing fluid, which may require additional wheel synchronization adding complexity to data analysis, compromising results accuracy with undesirable latency in the slow rotation of typical filter wheels, and rotation jitter.

What is needed is an optical computing device that may be manufactured to be tunable to weight wavelengths of light transmitted through, absorbed by, or reflected by a sample corresponding to analytes of interest that allows spectral measurements of samples using a broad spectral band with a reduced number of physical components.

DESCRIPTION OF ILLUSTRATIVE EMBODIMENTS

Illustrative embodiments and related methodologies are described below as they might be employed in an optical computing device and method that may include a detector having a plurality of structures with characteristics designed to weight predetermined wavelengths corresponding to analytes of interest. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies may become apparent from consideration of the following description and drawings.

Embodiments disclosed herein may include an optical computing device for use in optical measurement techniques in hydrocarbon exploration and extraction covering a wide spectral range involved in the measurement, including the ultraviolet (UV, 10 nm-350 nm), the visible (VIS, 350 nm-770 nm) and near infrared (NIR, 770 nm-2500 nm) to the mid-infrared spectral regions and beyond (MIR, 2.5 µm-50 µm). To provide detailed compositional information of a sample, some embodiments may include a tunable detector manufactured to cover an entire optical spectrum of interest, including the UV, VIS, NIR, and MIR spectral regions. In some embodiments, the tunable detector may be manufactured to respond to and weight light from a sample at predetermined wavelengths associated with or corresponding to analytes of interest.

Consistent with some embodiments, there is provided an optical computing device. The optical computing device may include an electromagnetic radiation source configured to produce electromagnetic radiation that optically interacts with a sample to produce sample-interacted light. The optical computing device may also include a tunable detector configured to respond to one or more predetermined wavelengths of the sample-interacted light, apply a weight based on an intensity of the response to the one or more wavelengths of the sample-interacted light, and generate a signal utilized for determining a characteristic of the sample.

Consistent with some embodiments, there is further provided an optical computing method including steps of irradiating a sample with electromagnetic radiation to produce sample-interacted light, addressing one or more cells of a tunable detector to tune the detector to respond to and weight one or more wavelengths of the sample-interacted light, the one or more wavelengths corresponding to one or more characteristics of the sample, generating a signal from the weighted one or more wavelengths of sample-interacted light incident on the tuned detector, and processing the generated signal to identify the characteristics of the sample.

Figure 1:
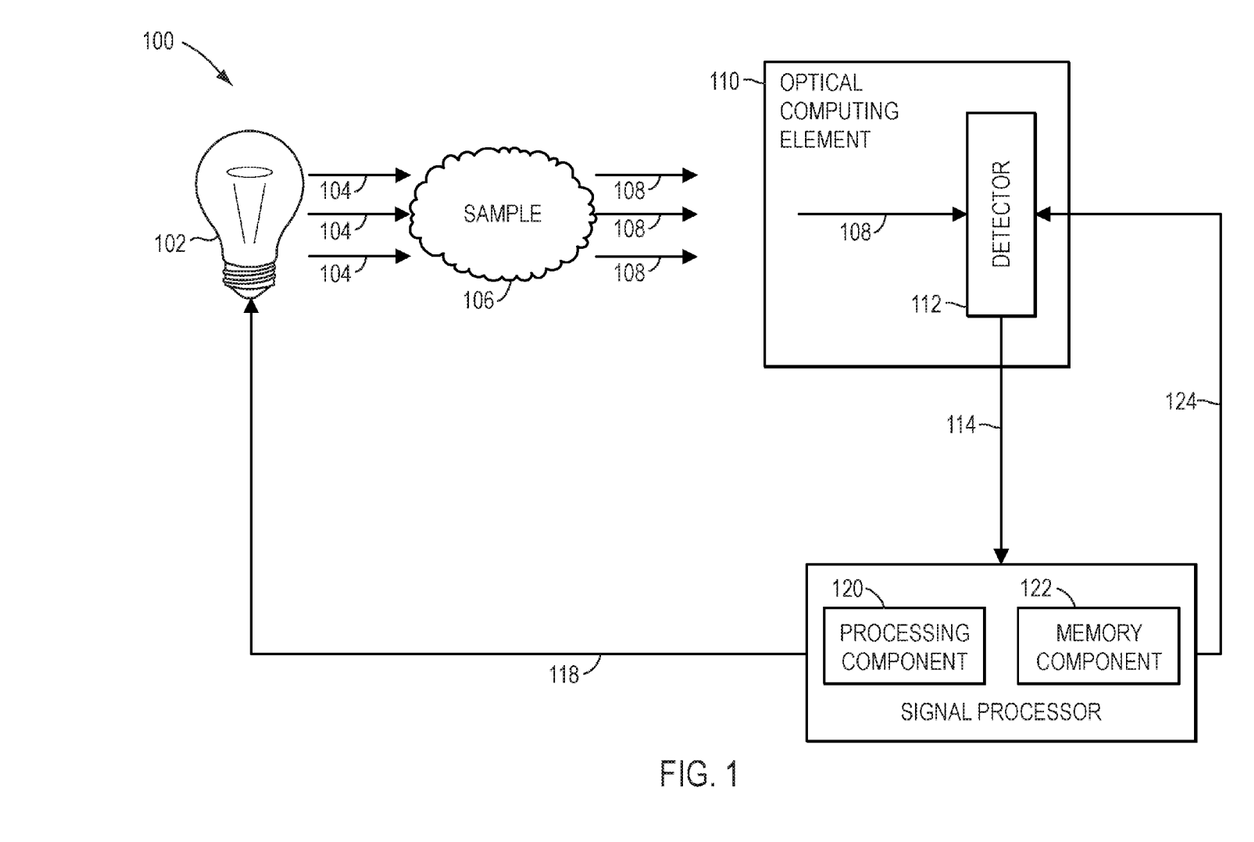
FIG. 1 is a block diagram illustrating an optical computing device, consistent with some embodiments.

FIG. 1 is a block diagram illustrating an optical computing device 100, consistent with some embodiments. As shown in FIG. 1, an electromagnetic radiation source 102 may be configured to emit or otherwise generate electromagnetic radiation 104. In some embodiments, electromagnetic radiation source 102 may be any device capable of emitting or generating electromagnetic radiation. For example, electromagnetic radiation source 102 may be a light bulb, UV light, vacuum UV light, light emitting device, laser, blackbody emitted from sample 106, photonic crystal, or X-Ray source, and the like. In one embodiment, electromagnetic radiation source 102 may be configured to optically interact with sample 106 and generate sample-interacted light 108 directed to an optical computing element 110.

In some embodiments, sample 106 may be any fluid, solid substance or material such as, for example, rock formations, concrete, other solid surfaces, etc. Although FIG. 1 shows electromagnetic radiation 104 passing through or incident upon sample 106 to produce sample-interacted light 108 (i.e., transmission mode or fluorescent mode), it is also contemplated herein to reflect electromagnetic radiation 104 off of sample 106 (i.e., reflectance mode), such as in the case of a sample 106 that is translucent, opaque, or solid, and equally generate sample-interacted light 108. Sample 106 may be provided to device 100 through a flow pipe or sample cell (not shown), for example, containing sample 106, whereby it is introduced to electromagnetic radiation 104. After being illuminated with electromagnetic radiation 104, sample 106 containing one or more analytes of interest (characteristics of sample 106, for example) produces an output of electromagnetic radiation (sample-interacted light 108, for example).

Although not specifically shown, one or more spectral elements may be employed in device 100 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after electromagnetic radiation source. Various other configurations and applications of spectral elements that may be employed, as will be understood by those ordinarily skilled in the art having the benefit of this disclosure.

In some embodiments, optical computing device 100 may be used to obtain values of a measurable property of sample 106 such as the concentration of an analyte of interest. An analyte of interest may be a hydrocarbon. In some embodiments, the measurable property may be an octane rating in a gasoline sample, or a GOR in a crude oil sample. Crude oil is a liquid containing a mixture of hydrocarbons forming oil, and dissolved gases such as methane $CH_4$, carbon dioxide, $CO_2$, and others. Hydrocarbons of interest in embodiments consistent with the present disclosure may also be any one of the group ethane, propane butane, pentane and hexane. The dissolved gases in naturally occurring crude hydrocarbons will form a gaseous phase at atmospheric conditions. Thus, when crude oil is released into the atmosphere it contains two main phases, a liquid phase which is the commonly known 'oil,' and a gas phase containing natural gas, including methane and other gases. Accordingly, the GOR of a downhole crude oil sample may indicate the value and potential use of a prospective reservoir.

Optical computing element 110 may be a variety of optical elements such as, for example, one or more optical elements or ICEs arranged or otherwise used in series in order to determine the characteristics of sample 106. In those embodiments using ICEs, the ICE may be configured to be associated with a particular characteristic of sample 106 or may be designed to approximate or mimic the regression vector of the characteristic in a desired manner, as would be understood by those ordinarily skilled in the art having the benefit of this disclosure. For example, optical computing element 110 may be configured to perform a prediction of a property of interest (C) in a sample by performing a dot product calculation between an optical spectrum (S) of the sample and an optical regression vector (b), as shown in the equation below:

$$C \propto S \cdot b \qquad (1)$$

Additionally, in an alternative embodiment, optical computing element 110 may function as both a beam splitter and computational processor, as will be understood by those same ordinarily skilled persons.

In general, optical computing device 110 may utilize optical elements to calculate the dot product of Eq. (1), as opposed to the hardwired circuits of conventional electronic processors. When electromagnetic radiation 102 interacts with sample 106, unique physical and chemical information about sample 106 may be encoded sample-interacted light 108 reflected from, transmitted through, or radiated from sample 106. This information may be a spectral "fingerprint" of sample 106. Thus, optical computing device 110 may be capable of extracting the information of the spectral fingerprint of multiple characteristics or analytes within "sample" and converting that information into a detectable output regarding the overall properties of sample 106.

In some embodiments, optical computing element includes a detector 112. Although detector 112 is shown as being part of optical computing element 110, in some embodiments, detector 112 may be separate from optical computing element 112. Detector 112 may be capable of detecting electromagnetic radiation, such as a photodetector, and may be a one or more tunable detectors or an array of tunable detectors arranged to be tuned or programmed to detect a particular analyte of interest by responding to and weighting wavelengths of light incident on detector 112, the weightings providing information related to the spectral fingerprint of sample 106. For example, detector 112 may be, but is not limited to, a semiconductor detector having a structure that may impart a particular optical spectral profile to detect an analyte of interest. Detector 112 may be configured to produce an output signal 114 in the form of a voltage or current that corresponds to the particular characteristic of the sample 106. For example, output signal 114 produced by detector 112 and the concentration of the characteristic of the sample 106 may be directly proportional based on the equation:

$$C = G(d) + O \qquad (2)$$

where C is the property of interest in the sample expressed as a product of output signal 114 produced by detector 112 ($d$) and a proportionality constant G and an offset O.

Detector 112 may be communicably coupled to a signal processor 116 such that a compensating signal 118 indicative of electromagnetic radiating deviations may be provided or otherwise conveyed thereto. Signal processor 116 may then be configured to computationally combine compensating signal 118 with output signal 114 to provide a more accurate determination of the characteristic of sample 106. In some embodiment, signal processor 116 may computationally combine compensating signal 118 with output signal 114 via multivariate statistical analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®), as will be understood by those ordinarily skilled in the art having the benefit of this disclosure.

In certain embodiments, signal processor 116 may include a processing component 120 and a memory component 122. Processing component 120 may be configured to process data received from detector 112 and provide signals to electromagnetic radiation source 102 and back to detector 112 upon executing commands stored in memory component 122. In some embodiments, processing component 120 may provide an electronic adjustment signal 124 to detector 112 to tune or program detector 112 to respond to and weight certain wavelengths of sample-interacted light 108 corresponding to one or more analytes of interest. In some embodiments, electronic adjustment signal 124 may be a signal that addresses one or more cells or sub-cells of detector 112, wherein each of the cells or sub-cells of detector 112 have structures with characteristics manufactured to absorb or transmit light at certain wavelengths, and provide a weighted value based on the absorption or transmission of light at a wavelength. As used herein a "weight" of light at certain wavelengths may refer to a degree to which detector 112, or structures of detector 112, respond to the incident light. The weight or weighting may be a value associated with the absorption or transmission of light. For example, in some embodiments, a weight between 0 and 1 may be assigned based on the amount of light absorbed or transmitted by the structures at a particular wavelength. In some embodiments, processing component 120 may be one or more processors, micro-controllers, graphics processing units (GPUs) or digital signal processors (DSPs), and memory component 122 may correspond to a random access memory (RAM), an internal memory component, a read-only memory (ROM), or an external or static optical, magnetic, or solid-state memory, and a combination thereof.

In some embodiments, detector 112 may be tuned with multiple optical spectrums. Each optical spectrum may interact with the spectrum of one or more analytes of interest, often functioning as the dot or inner product, such that output signal 114 may be dominantly contributed by the summation of the product of each peak portion of optical spectrum and the corresponding portion of analyte spectrum at the same wavelength in accordance with Eqs. (1) and (2). In some embodiments, the magnitude variations of peaks may represent the strength or intensity of the weightings and correspond to the value of output signal 114. The spectrum of interest of a given characteristic of sample 106 may include any number of different wavelengths. In some embodiments, detector 112 may be combined with an ICE however, in other embodiments, detector 112 may replace an ICE and act as the ICE of optical computing device 110.

Figure 2A:
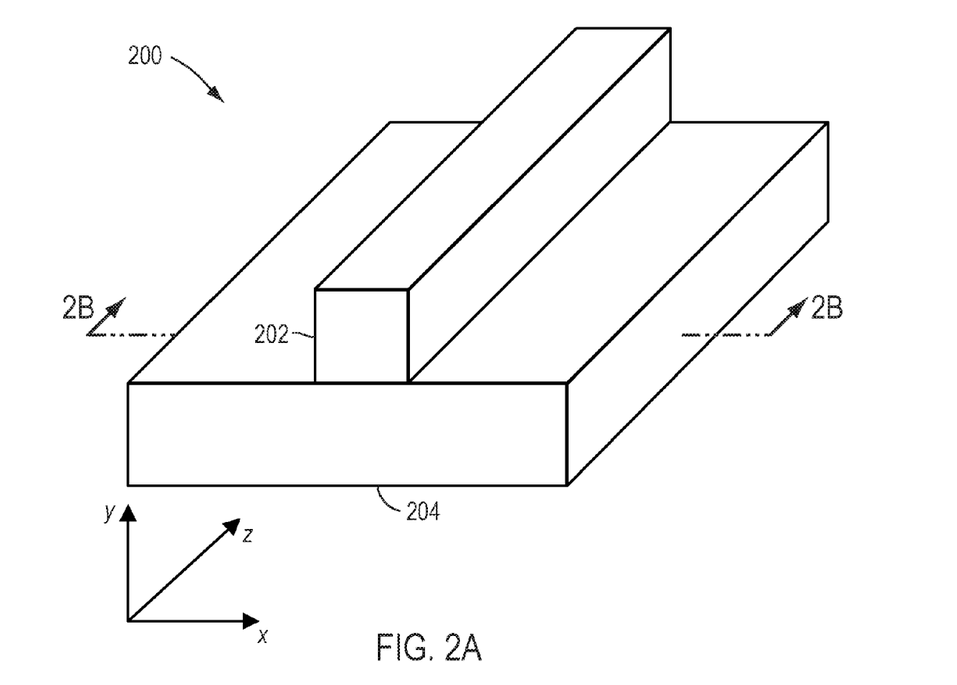
FIG. 2A is a diagram illustrating a three-dimensional structure of a detector.
Figure 2B:
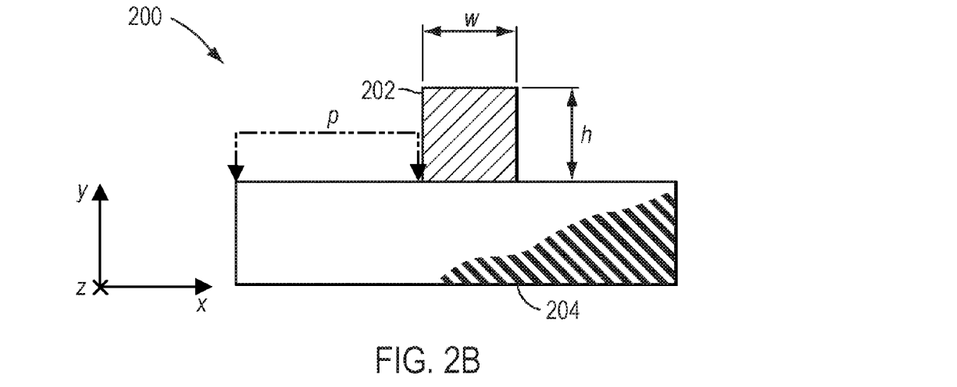
FIG. 2B is a cross-section taken at II-II', consistent with some embodiments.

FIG. 2A is a diagram illustrating a three-dimensional structure of detector 112, and FIG. 2B is a cross-section taken at II-II', consistent with some embodiments. As shown in FIG. 2A, detector 112 may have a multi-dimensional structure 200 that includes one or more semiconductor ridges, protrusions, or fins 202 formed on a substrate 204. In some embodiments, fin 202 may be made from a semiconductor material such as silicon, Germanium (Ge), Gallium Arsenide (GaAs), and Indium Gallium Arsenide (InGaAs). Moreover, substrate 204 may also be a semiconductor substrate or a dielectric or other insulator substrate and, in some embodiments, may be a $SiO_2$ substrate. In some embodiments, structure 200 of detector 112 may be manufactured according to known semiconductor manufacturing techniques. For example, a layer of a first semiconductor material may be deposited on a substrate made from a second semiconductor material. The first semiconductor material may then be patterned to form fin 202 on substrate 204. In some embodiments, the patterning may be achieved through etching, masked deposition and the like. As another example, substrate 204 may be a silicon-on-insulator wafer having a silicon layer over an insulating layer, wherein the silicon layer is patterned to form fin 202. Although not shown in FIG. 2A, structure 200 may include multiple fins 202 spaced apart from each other at a predetermined pitch p.

As shown in FIG. 2B, fin 202 may be formed or manufactured to have a specific width w, a specific height h, and to have a specific pitch p between adjacent fins 202 (not shown) on substrate 204. In some embodiments, light such as sample-interacted light 108, may be incident on structure 200 of detector 112, and the width w, height h, pitch p, and material of fins 202 may determine wavelengths of the incident light that may be weighted. That is, the wavelengths $\lambda$ weighted by fins 202 on structure 200 of detector 112 may be dependent on the width w, height h, pitch p, and material of fins 202. Consequently, in some embodiments, the width w, height h, and pitch p of fins 202 in structure 202 may be controlled during the manufacture of structure 200 so that structure 200 of detector 112 responds to and weights one or more particular wavelengths $\lambda$, an example of which may be shown in FIG. 5. These weighted wavelengths $\lambda$ may correspond to one or more analytes of interest.

Figure 3A:
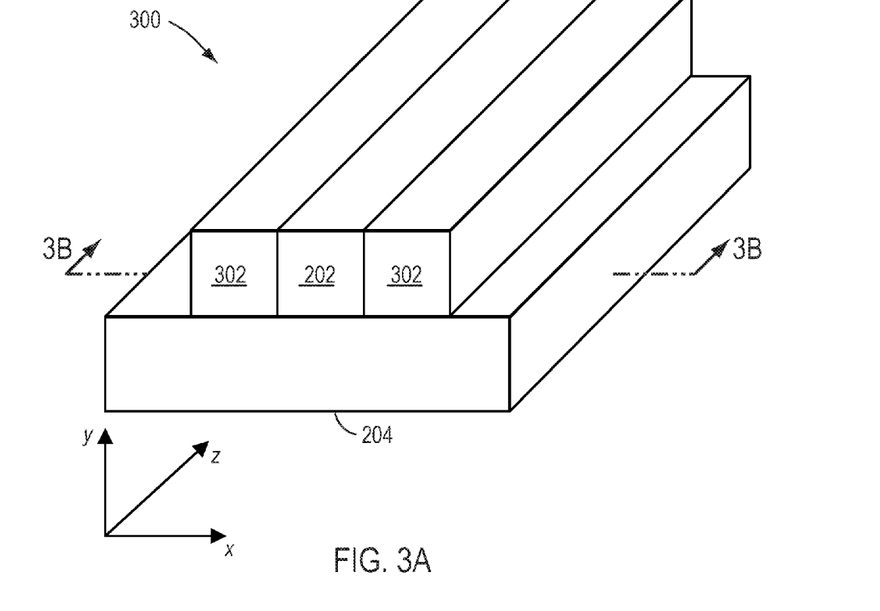
FIG. 3A is a diagram illustrating a three-dimensional structure of a detector.
Figure 3B:
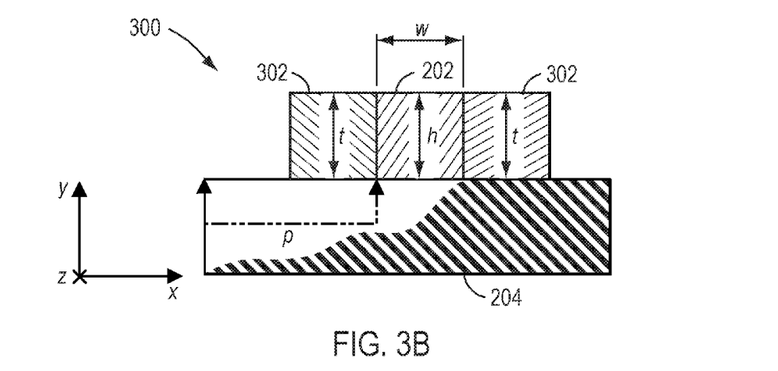
FIG. 3B is a cross-section taken at III-III', consistent with some embodiments.

FIG. 3A is a diagram illustrating a three-dimensional structure 300 of detector 112, and FIG. 3B is a cross-section taken at III-III', consistent with some embodiments. As shown in FIG. 2A, detector 112 may have a structure 300 that includes one or more semiconductor ridges, protrusions, or fins 202 formed on a substrate 204, similar to structure 200 shown in FIGS. 2A and 2B. However, structure 300 shown in FIGS. 3A and 3B includes one or more metal ridges 302 surrounding fin 202. In some embodiments, metal ridges 302 may be made from a conductive metal, such as gold (Au) or silver (Ag), or any metallic reflecting material. Structure 300 may be manufactured according to known semiconductor manufacturing techniques. In some embodiments, fin 202 may be formed after forming metal ridges 302 such that metal ridges 302 may be used to align fin 202. Alternatively, metal ridges 302 may be formed after forming fin 202 such that metal ridges 302 are aligned to fin 202.

As shown in FIG. 3B, metal ridges 302 may have a thickness t. In some embodiments, thickness t may approximately the same as height h of fin 202. In some embodiments, light such as sample-interacted light 108, may be incident on structure 300 of detector 112, and the material and thickness t of metal ridges 302, along with the width w, height h, pitch p, and material of fin 202, may determine wavelengths λ of the incident light that may be responded to by structure 300 and weighted. That is, the wavelengths λ that structure 300 responds to and produces a certain associated weighting may be dependent on the material and thickness t of metal ridges 302 along with the width w, height h, pitch p, and material of fin 202. Consequently, in some embodiments, the thickness t and material of metal ridges 302, and the width w, height h, and pitch p of fin 202 may be selected and/or controlled during the manufacture of detector 112 to tune detector 112 to be able to respond to and weight one or more wavelengths λ, an example of which may be shown in FIG. 5. These wavelengths λ and the corresponding weights may correspond to one or more analytes of interest.

Figure 4A:
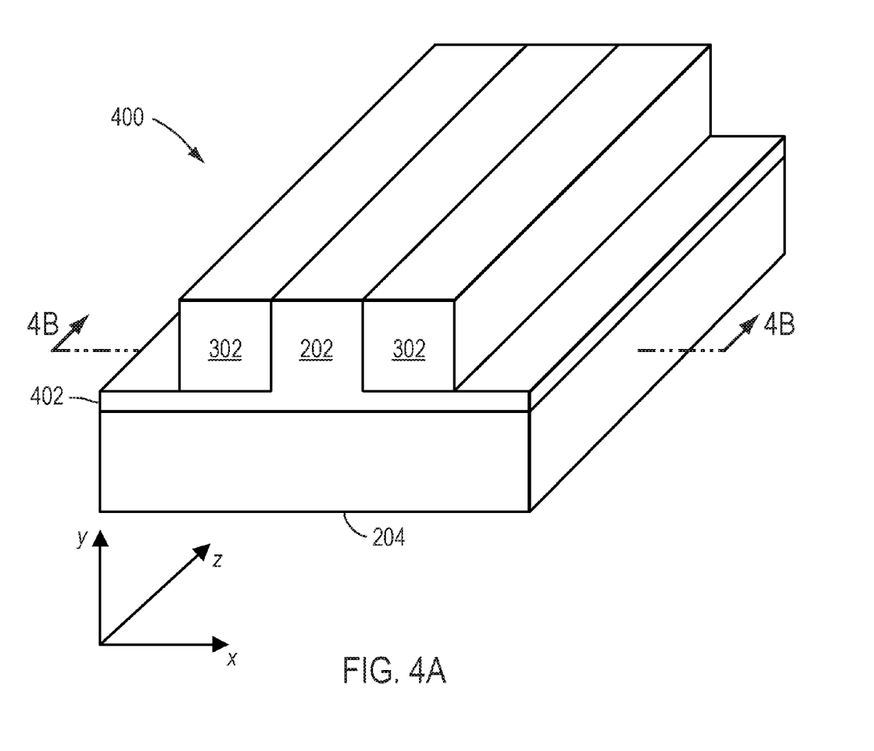
FIG. 4A is a diagram illustrating a three-dimensional structure of a detector.
Figure 4B:
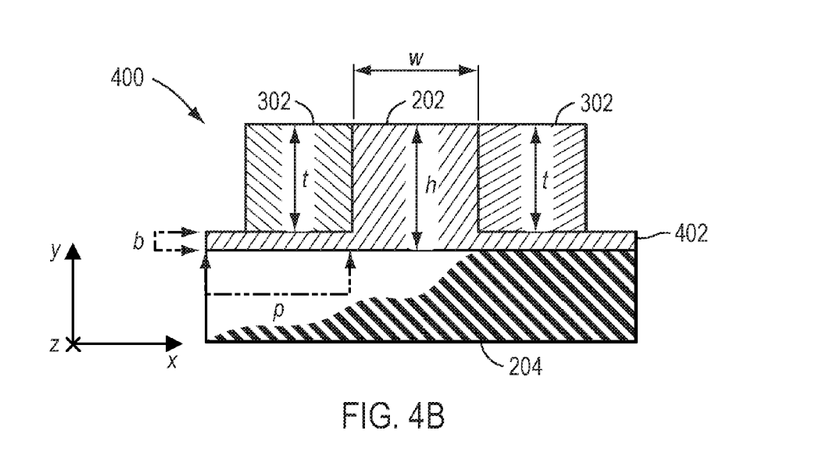
FIG. 4B is a cross-section taken at IV-IV', consistent with some embodiments.

FIG. 4A is a diagram illustrating a three-dimensional structure 400 of detector 112, and FIG. 4B is a cross-section taken at IV-IV', consistent with some embodiments. As shown in FIG. 4A, detector 112 may have a structure 400 that includes one or more semiconductor ridges, protrusions, or fins 202 formed on a substrate 204, similar to structure 200 shown in FIGS. 2A and 2B. Structure 400 may also include metal ridges 302, similar to structure 300. Moreover, structure 400 may also include a semiconductor base layer 402 formed on substrate 204. Base layer 402 may be a thin layer of silicon in some embodiments. Structure 400 may be manufactured according to known semiconductor manufacturing techniques. For example, semiconductor base layer 402 may be formed on substrate 204 as a silicon-on-insulator (SOI) wafer.

As shown in FIG. 4B, base layer 402 may have a base thickness b. In some embodiments, light such as sample-interacted light 108, may be incident on structure 400 of detector 112, and the base thickness b of base layer 402, along with the material and thickness t of metal ridges 302, and the width w, height h, pitch p, and material of fins 202, may determine wavelengths λ of the incident light that may be responded to be structure 400 and correspondingly weighted. That is, the wavelengths λ responded to and the weighting by structure 400 of detector 112 may be dependent on the base thickness b, along with the material and thickness t of metal ridges 302 and the width w, height h, pitch p, and material of fins 202. Consequently, in some embodiments, the base thickness b of semiconductor base 402, the thickness t and material of metal ridges 302, and the width w, height h, and pitch p of fins 202 may be selected and/or controlled during the manufacture of detector 112 to tune detector 112 to be able to respond to and weight one or more wavelengths λ, an example of which may be shown in FIG. 5. These wavelengths λ and their corresponding weights may correspond to one or more analytes of interest.

In some embodiments, semiconductor base 402 may act as a waveguide clad by substrate 204 at the bottom and metal ridges 302 at the top. When light, for example sample-interacted light 108, is incident on detector 112 having structure 400, the light may be coupled into the wave guide formed by semiconductor base 402, substrate 204 and metal ridges 302 to provide additional loss channels for the resonating body formed by structure 400, which may lower the Q-factor of the resonance and increase the absorption cross-section, also increasing the responsivity of detector 112. This is further described in Balram et al., "Self-aligned silicon fins in metallic slits as a platform for planar wavelength-selective nanoscale resonant photodetectors," Optics Express, Vol. 20, No. 20, 24 Sep. 2012, pages 22735-22742, which is hereby incorporated by reference.

Figure 5:
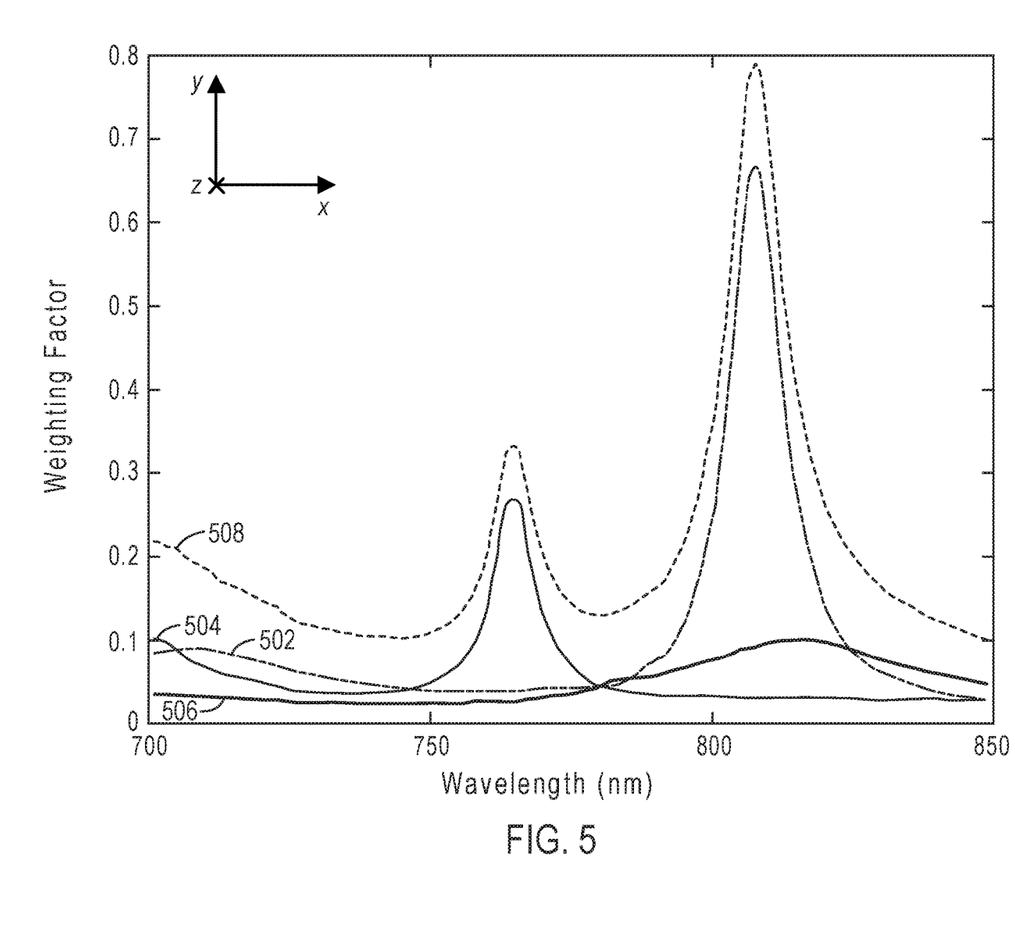
FIG. 5 shows response spectra of a detector, consistent with some embodiments.

FIG. 5 shows the response spectra 502, 504, and 506 broad band light from the electromagnetic radiation source 104 incident on structures 200, 300, and 400 of detector 112, consistent with some embodiments. The ordinate axis in FIG. 5 corresponds to a weighting factor of light from a cross-section of detector 112. The abscissa axis in FIG. 5 corresponds to a wavelength λ of light 104. The spectral region covered by the abscissa in FIG. 5 may be the UV, VIS, NIR, MIR spectral region or any combination of the above.

As shown in FIG. 5, a detector 112 having fin 202 of a predetermined height h and width w may be sensitive to or weight light at a particular wavelength λ. Moreover, as further shown in FIG. 5, the wavelength λ of the light responded to and weighted by structure 200 may be changed based on the structure surrounding fin 202. For example, for a detector 112 having structure 200 with fin 202 having a height h of 120 nm and a width w of 550 nm, the incident light may be weighted at a wavelength λ of about ~700 nm by a factor of 0.1, and the incident light may be weighted at a wavelength λ between about ~810 nm and ~820 nm to a factor of 0.1, as shown in optical spectrum 502.

The optical response may be modified with structure 300. As shown in FIG. 5, structure 300, having the same size fin 202, weights the incident light to about 0.3 at a wavelength λ of about ~770 nm, as shown by optical spectrum 504. This optical response may be further modified by structure 400. Structure 400 having the same size fin 202 may weight the incident light to about 0.67 at a wavelength λ of about ~800 nm, as shown by optical spectra 506. In some embodiments, a detector 112 may include each of structures 200, 300, and 400, in equal ratios to obtain a summed or combined optical response that includes each of the optical responses of the individual structures. For example, a detector 112 having each of structures 200, 300, and 400 in equal ratios may weight the incident light to about 0.22 at a wavelength λ of about ~700 nm, about 0.3 at a wavelength λ of about ~770 nm, and about 0.8 at a wavelength of about ~800 nm, as shown by optical spectrum 508. In some embodiments, the materials of substrate 200, fin 202, metal ridges 302, and semiconductor base layer 402 may be changed in order to achieve different responses and weights. Further, the height h, width w, and pitch p of fin 202, the thickness t of metal ridges 302, as well has the height b of semiconductor base layer 402 may all be changed to achieve optical responses at different wavelengths. Consequently, detector 112 may be manufactured having a variety of structures and sizes of structures to be able to weight light at multiple wavelengths in order to detect analytes of interest.

Figure 6:
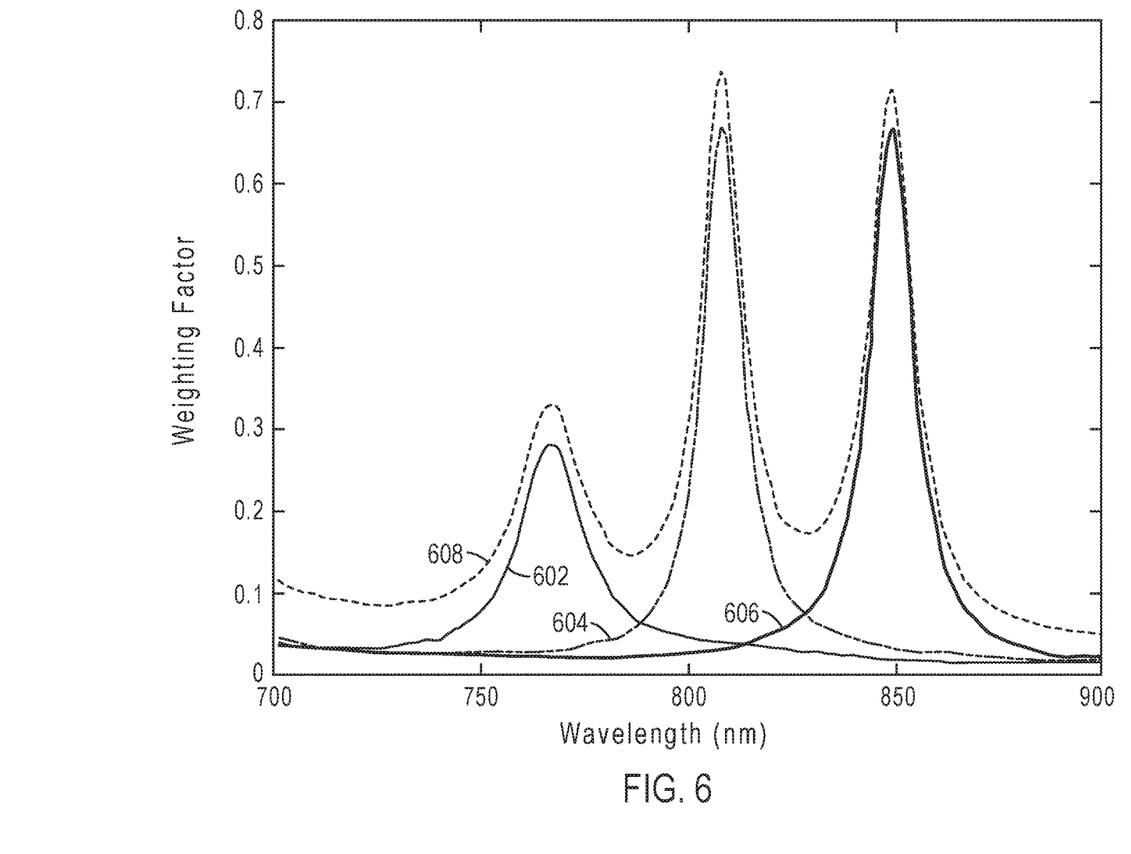
FIG. 6 shows response spectra of a detector having fins of different widths, consistent with some embodiments.

FIG. 6 shows the response spectra 602, 604, 606, and 608 of broad band light from the electromagnetic radiation source 104 incident on detector 112 having fins 202 of different widths w, consistent with some embodiments. The ordinate axis in FIG. 6 corresponds to a weighting factor of light from a cross-section of detector 112. The abscissa axis in FIG. 6 corresponds to a wavelength λ of incident light 104. The spectral region covered by the abscissa in FIG. 6 may be the UV, VIS, NIR, MIR spectral region or any combination of the above.

In some embodiments, the width w of fins 202 may be resonantly tuned to weight a wavelength λ may be about w≈(N+1) λ/2n, wherein N is an integer=0, 1, 2, 3 . . . , n is an index associated with the material of fins 202, and λ is a wavelength of light responded to and weighted by fin 202. For the example shown in FIG. 6, the width w was determined based on the equation w≈5λ/2n$_{si}$ for fins 202 made from silicon. As shown in FIG. 6, the calculated sensitivity for detector 112 having fin 202 of widths w of 500 nm, 550 nm, and 600 nm, a fin 202 height h of 120 nm, and a base layer 402 thickness b of 50 nm demonstrates a shift to longer wavelengths as the width w of fins 202 are increased. When width w of fins 202 is 500 nm, the light incident on fins 202 may be weighted to a factor of about 0.3 by fin 202 at a resonant wavelength near ~770 nm, as shown in response spectrum 602. Similarly, when width w of fin 202 is 550 nm, light incident on fin 202 may be weighted by a factor of about 0.67 by fin 202 at a resonant wavelength near ~800 nm, as shown in response spectrum 604. Further, when width w of fin 202 is 600 nm, light incident on fin 202 may be weighted by a factor of about 0.67 at a resonant wavelength near ~850 nm, as shown in response spectrum 606.

As further shown in FIG. 6, a detector 112 having structures including fins 202 of widths w of 500 nm, 550 nm, and 600 nm, in equal ratios may obtain a response that includes weighting factors of about 0.32 of light at a resonant wavelength λ of about ~770 nm, about 0.72 of light at a resonant wavelength λ of about ~800 nm, and about 0.70 of light at a resonant wavelength λ of about ~850 nm, as shown in response spectrum 608, which may be a combination of response spectra 602-606. That is, detector 112 having multiple fins 202 of varying widths w, may be able to obtain a response from incident light 104 that includes weightings at multiple wavelengths λ. Consequently, detector 112 may be constructed to have fins 202 of predetermined widths w in order to obtain a response for an analyte of interest that corresponds to the predetermined widths w. In some embodiments, response spectra 602-606, and the combination spectrum 608 may correspond to the regression vector b shown in Eq. (1).

Figure 7:
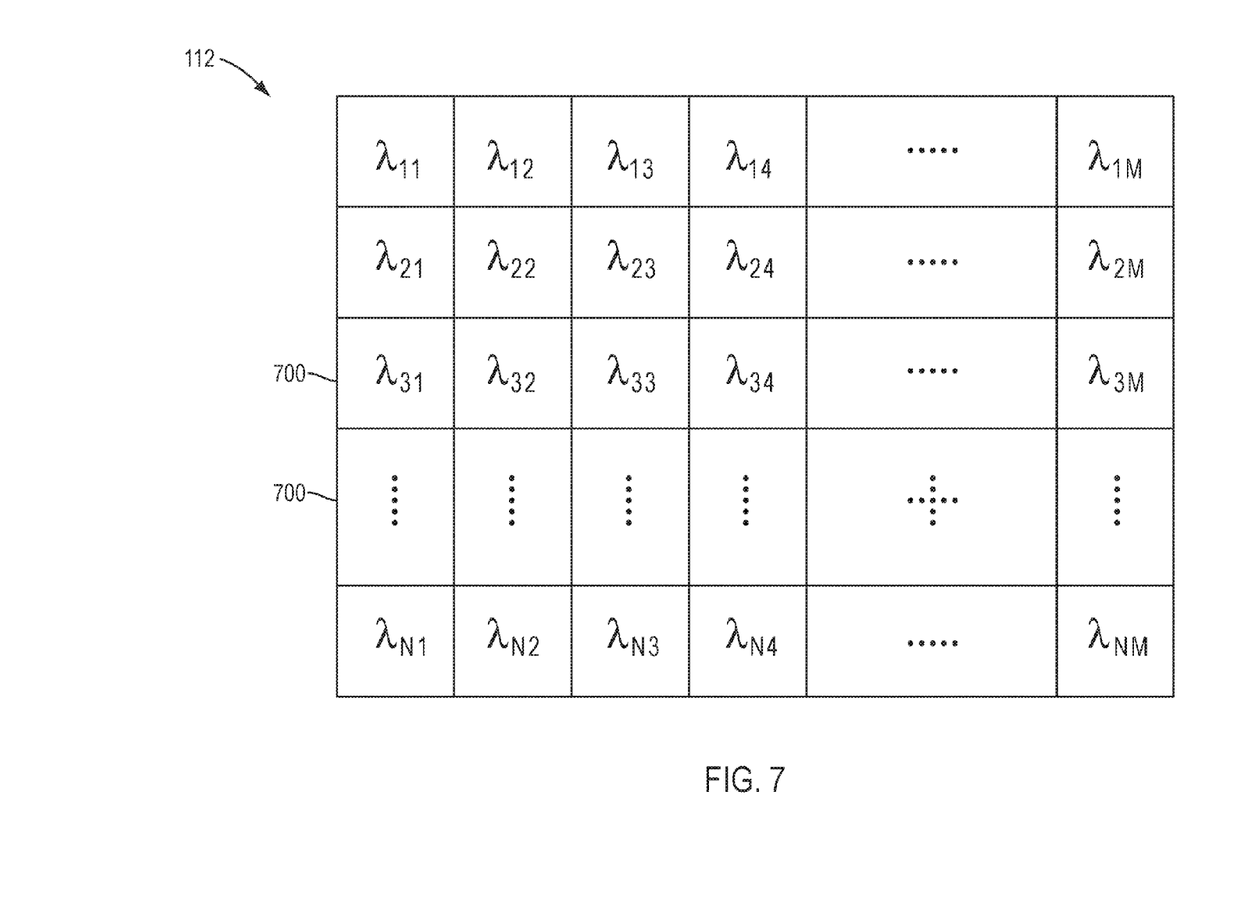
FIG. 7 is a diagram illustrating a detector having addressable cells responding to a predetermined wavelength λ, consistent with some embodiments.

FIG. 7 is a diagram illustrating detector 112 having addressable cells 700 responding to a predetermined wavelength λ, consistent with some embodiments. As shown in FIG. 7, detector 112 may be manufactured to have M×N addressable cells that may each respond to a predetermined wavelength λ. In some embodiments, each of the cells 700 may include a structure including fins 20 having a predetermined width w, where the width w is chosen such that fin 202 weights a particular wavelength λ of incident light, such as shown in FIG. 6. In some embodiments, each of the cells may include one of structures 200, 300, or 400, capable of responding to and applying or assigning a particular weighting to a predetermined wavelength λ of incident light, such as shown in FIG. 5. In further embodiments, detector 112 may include cells 700 that have a combination of structures such as structures 200, 300, and 400, and fin 202 having widths w, heights h, and pitches p that are chosen to respond to and weight a particular wavelength λ. Further, the materials of metal ridges 302, substrate 204, base layer 402 and fin 202 may be chosen to weight a particular wavelength λ. In addition, the thickness t of metal ridges 302 and the thickness b of base layer 402 may be chosen to respond to and weight a particular wavelength λ. In general, each cell 700 may include a structure that has characteristics appropriate for weighting a particular wavelength λ.

In some embodiments, each of the M×N addressable cells may be addressed using standard integrated circuit techniques such that one or more of the cells are addressed at a time. In some embodiments, cells 700 may be addressable by processing component 120 of signal processor 116 via signal 124. For example, FIG. 7 illustrates that detector 112 may be selectively addressed to respond to and weight wavelengths $\lambda_{12}$, $\lambda_{31}$, $\lambda_{23}$, and $\lambda_{34}$. As a result, detector 112 may receive sample-interacted light 108 and provide a response based on the weighting of wavelengths $\lambda_{12}$, $\lambda_{31}$, $\lambda_{23}$, and $\lambda_{34}$, which may correspond to an analyte of interest. Other analytes of interest may correspond to other combinations of wavelength responses such that detector can be programmed or tuned by addressing cells 700 manufactured to respond to and weight the particular wavelengths corresponding to the analyte of interest. In some embodiments, cells 700 may be addressed in the field allowing for quick tuning or programming of detector 112 for detecting analytes of interest.

In some embodiments, cells 700 may be addressed to respond to and weight wavelengths corresponding to a spectral signature of one or more analytes of interest, which may then be reflected in output signal 114, such that detector 112 effectively performs the dot product of sample-interacted light 108 and regression vectors related to wavelength absorbed by cells 700 and produces an output signal 114 proportional to the property of interest, such as an analyte of interest. Processing component 120 may then use output signal 114 to determine the property of interest using instructions stored in memory component 122. In some embodiments, detector 112 may have cells 700 having a size and number that may be optimized to maximize a signal-to-noise ratio (SNR). In some embodiments, each cell 700 may be about 1 μm by 1 μm.

Optical computing device 100 having detector 112 as described herein may be configured to detect not only the composition and concentrations of a material or mixture of materials such as sample 106, but they also can be configured to determine physical properties and other characteristics of the material as well, based on their analysis of the electromagnetic radiation received from sample 106. For example, optical computing device 100 having detector 112 may be configured to determine the concentration of an analyte and correlate the determined concentration to a characteristic of a substance by processing component 120. As will be appreciated, optical computing device 100 having detector 112 may be configured to detect as many characteristics or analytes as desired in sample 106 by addressing cells 700 specifically manufactured to respond to and weight wavelengths of light corresponding to the characteristics or analytes. In some embodiments, the properties of a substance can be a combination of the properties of the analytes therein (e.g., a linear, non-linear, logarithmic, and/or exponential combination). Accordingly, the more characteristics and analytes that are detected and analyzed using optical computing device 100, the more accurately the properties of sample 106 can be determined.

Figure 8:
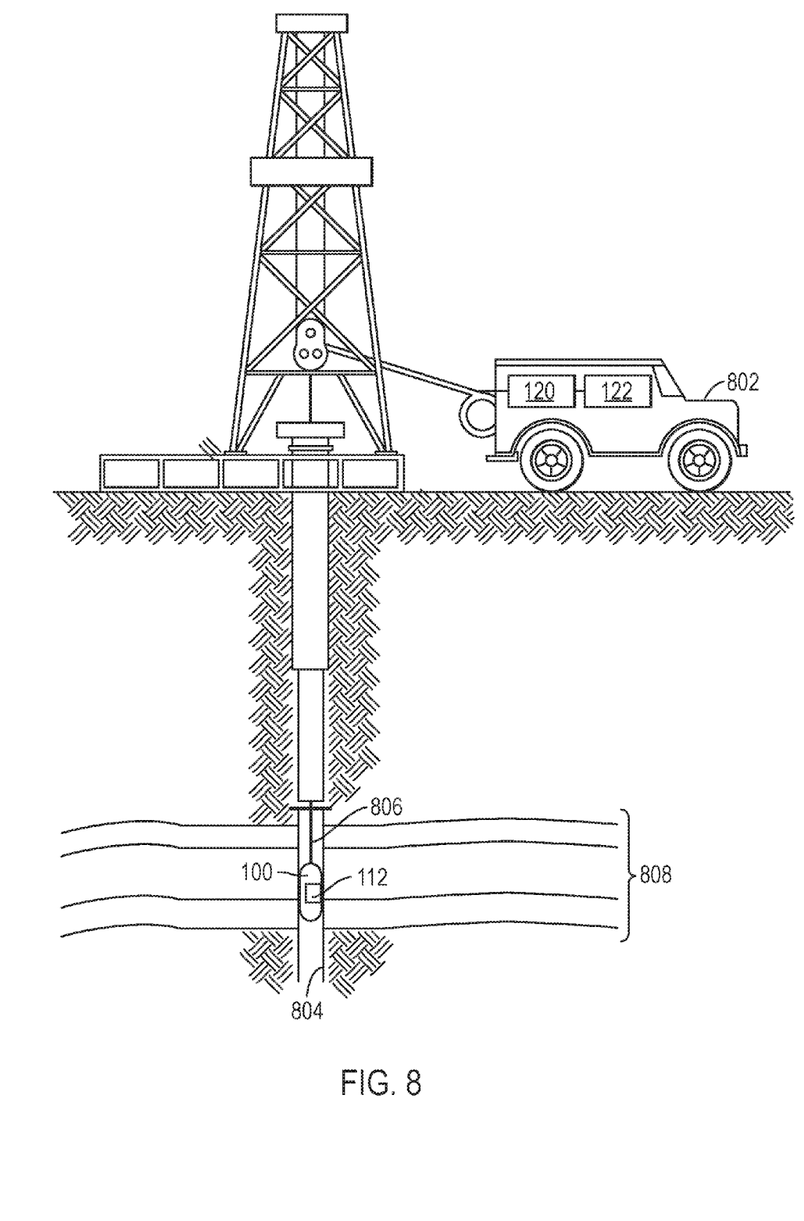
FIG. 8 shows an optical computing device having a tunable detector for measuring an analyte of interest in a wireline logging application, according to some embodiments.

FIG. 8 shows an optical computing device 100 having tunable detector 112 for measuring an analyte of interest in a wireline logging application, according to some embodiments. Wireline logging performs measurements of fluids and substrates in wellbores drilled for oil and hydrocarbon exploration. In some embodiments, a movable unit 802 includes a processing component 120 and memory component 122 to provide commands for optical computing device 100 to perform measurements and store data obtained from the measurements. Accordingly, once a wellbore 804 has been drilled, a wireline logging measurement may be performed by introducing optical computing device 100 into wellbore 804, using a wireline 806. Wellbore 804 may traverse a ground formation 808. Optical computing device 100 may include tunable detector 112, as disclosed herein. Furthermore, optical computing device 100 may include electromagnetic radiation source 102, such as shown in FIG. 1. In some embodiments, a portion of electromagnetic radiation source 102 may be included in movable unit 802, such as a laser device, or an illumination lamp. In some embodiments, electromagnetic radiation source 102 and optical computing device 100 may include an optical fiber, or fiber bundle. The optical fiber or fiber bundle may carry electromagnetic radiation, including light signals, along wireline 806.

Figure 9:
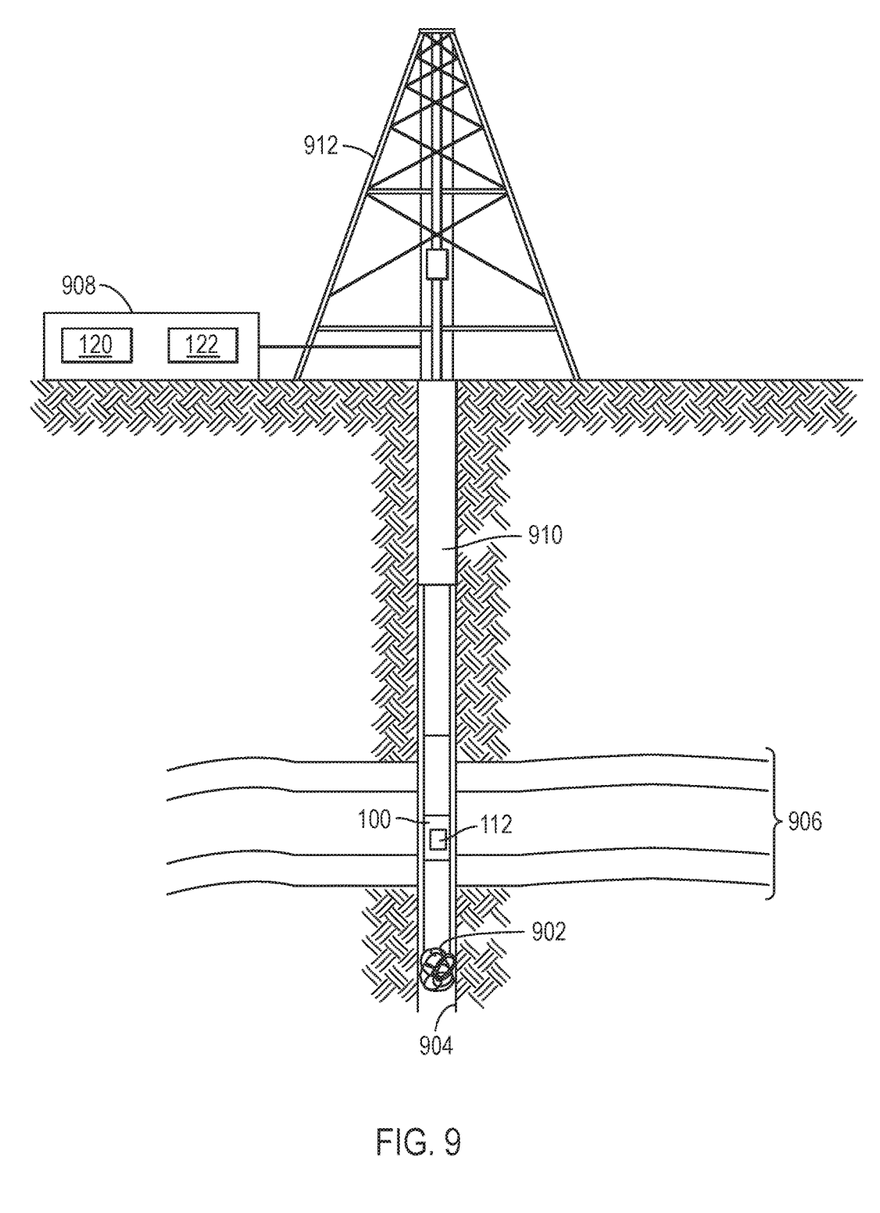
FIG. 9 shows a drill bore including optical computing device having a tunable detector for measuring properties of a sample in a logging-while-drilling (LWD) application, according to some embodiments.

FIG. 9 shows a drill bore including optical computing device 100 having tunable detector 112 for measuring properties of a sample in a logging-while-drilling (LWD) application, according to some embodiments. An LWD configuration logs acoustic data while a wellbore is being drilled. As shown in FIG. 9, a bottom hole assembly includes a drill 902 to form a wellbore 904. In some embodiments, wellbore 904 may traverse a ground formation 906. Drill 902 may be operated by a controller 908 through drill string 910. A drilling rig 912 provides structural support to drill string 910. Controller 908 may include processing component 120 and memory component 122, in some embodiments. Memory component 122 may store commands and data used by processing component 120 to control the bottom hole assembly. Controller 908 may also operate optical computing device 100 included in drill 904. In some embodiments, optical computing device 100 may include tunable detector 112 for measuring one or more characteristics or properties of a sample of ground formation 906 in an LWD application. Furthermore, optical computing device 100 may include electromagnetic radiation source 102, such as shown in FIG. 1. In some embodiments, a portion of electromagnetic radiation source 102 may be included in movable unit 802, such as a laser device, or an illumination lamp. Accordingly, in LWD applications as depicted in FIG. 9, optical computing device 100 may transmit and receive data from controller 908 using signals traveling through the drilling mud, or an acoustic telemetry device, or a wired pipe configuration.

In some embodiments, optical computing device 100 including tunable detector 112 as disclosed herein may be implemented in permanent monitoring applications. For example, in an oil extraction rig similar to drilling rig 912, tunable detector 112 may be configured to determine the chemical composition of the extracted hydrocarbons during regular operations. Further according to some embodiments, an optical computing device 100 including tunable detector 112 may be used in a subsea environment of a wireline operation, an LWD operation, or a permanent monitoring operation.

Figure 10:
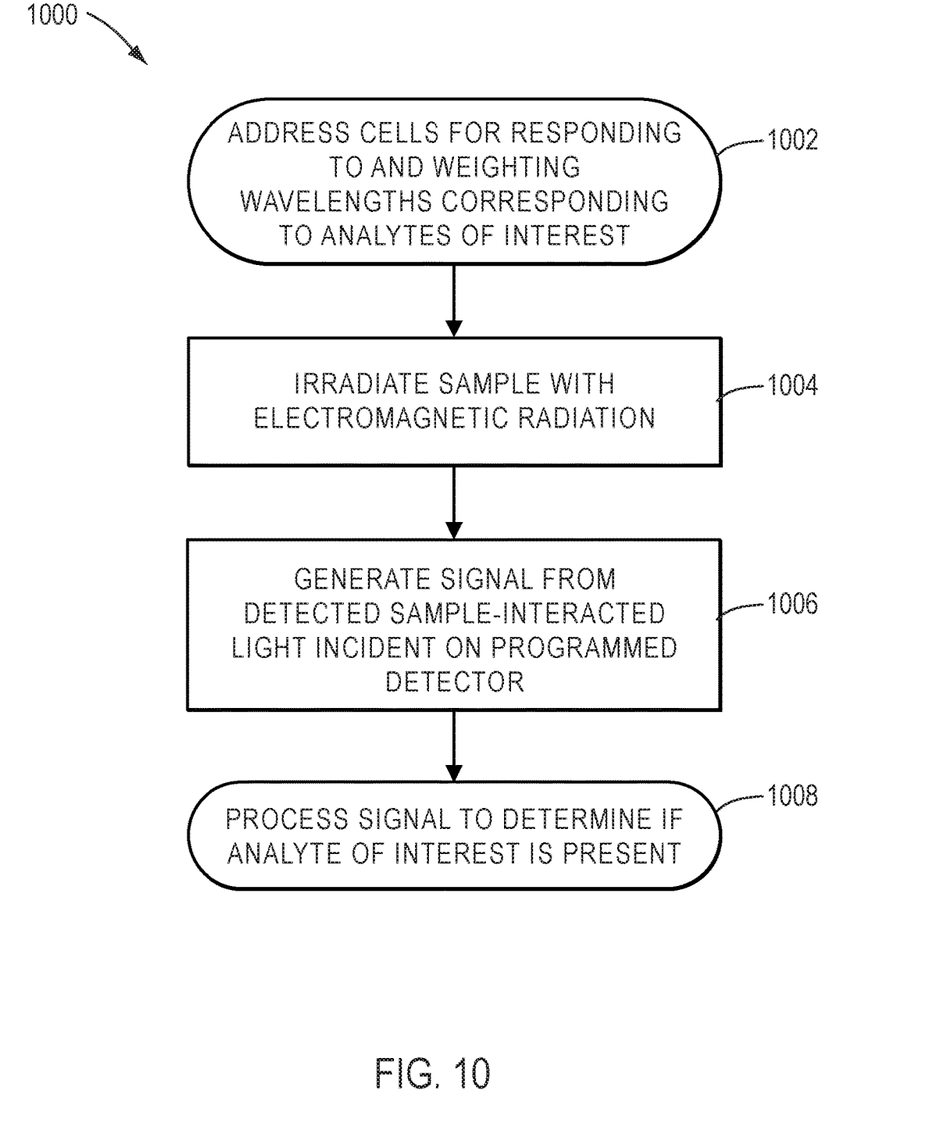
FIG. 10 is a process for determining if sample includes one or more analytes of interest, consistent with some embodiments.

FIG. 10 is a process 1000 for determining if sample 106 includes one or more analytes of interest, consistent with some embodiments. In some embodiments, one or more steps of process 1000 may be performed by optical computing device 100, and may be performed in a downhole application or an LWD application. Moreover, memory component 122 may include instructions that, when executed by one or more processors of processing component 120, may cause process 1000 to be performed. As shown in FIG. 10, process 1000 may begin by addressing cells 700 of detector 112 for responding to and weighting wavelengths corresponding to analytes of interest (1002). In some embodiments, detector 112 may be a tunable detector including non-planar semiconductor structures, such as structures 200, 300, and 400 including fin 202, substrate 204, metal ridges 302, and base layer 402. In some embodiments, detector 112 may have combinations of structures 200, 300, and 400, wherein one or more of the non-planar semiconductor structures make up a cell 700. Moreover, the structures making up cells 700 may have characteristics, such as a width w, height h, pitch p, and material of fin 202, a thickness t and material of metal ridges 302, a thickness b and material of base layer 402, and material of substrate 204 that have been chosen and optimized to respond to and weight particular wavelengths. Cells 700 may be addressed by signal 124 to be active to program or tune detector 112 to respond to and weight certain wavelengths that correspond to the analytes of interest.

Sample 106 may then be irradiated with electromagnetic radiation 104 from electromagnetic radiation source 102 (1004). In some embodiments, electromagnetic radiation source 102 may be any device capable of emitting or generating electromagnetic radiation. For example, electromagnetic radiation source 102 may be a light bulb, UV light, vacuum UV light, light emitting device, laser, blackbody emitted from sample 106, photonic crystal, or X-Ray source, and the like. In one embodiment, electromagnetic radiation 102 may be configured to optically interact with sample 106 and generate sample-interacted light 108. Detector 112 may then generate signal 114 from detected sample-interacted light 108 incident on the programmed detector 112 (1006). In some embodiments, certain wavelengths of sample-interacted light 108 incident on programmed detector 112 may be weighted by addressed cells 700 having structures configured or manufactured to respond to those wavelengths, and a signal 114 related to the weighting may be generated by detector 112 and transmitted to signal processor 116. Signal processor 116 may then process signal 114 to determine if one or more analytes of interest are present in sample 106 (1008). In some embodiments, processing component 120 may execute instructions stored in memory component 122 to process signal 114 and determined if the one or more analytes are present based on the relation of signal 114 to the wavelengths and their weighting.

Those ordinarily skilled in the art having the benefit of this disclosure will realize the aforementioned optical computing devices are exemplary in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, optical computing device 100 may comprise a parallel processing configuration whereby sample-interacted light 108 is split into multiple beams. The multiple beams may then simultaneously go through corresponding optical computing elements 110 including corresponding tunable detectors 112, whereby multiple analytes of interest are simultaneously detected. In other embodiments, optical computing device 100 may utilize two substantially different light sources (UV and IR, for example) to cover the optical activity of all the analytes of interest (i.e., some analytes might be only UV active, while others are IR active). Those ordinarily skilled in the art having the benefit of this disclosure will realize the choice of a specific optical configuration is mainly dependent upon the specific application and analytes of interest.

Embodiments described herein may provide a system and method for performing optical calculations for determining information related to one or more properties of interest of a sample that uses fewer parts and may be more compact and easier to manufacture. Some embodiments described herein may utilize a programmable or tunable detector that includes structures designed and manufactured to respond to and weight certain wavelengths of light from a sample that correspond to properties related to the sample. This programmable or tunable detector may be used along with an ICE to provide an enhanced determination or may be used as the computing element taking the place of standard ICEs. Moreover, some embodiments described herein may include an array of tunable or programmable detectors that may be addressable and programmed to respond to and weight a wide spectrum of light through a sample to determine significant information about the sample.

Embodiments described herein further relate to any one or more of the following paragraphs:

1. An optical computing device, comprising: an electromagnetic radiation source configured to produce electromagnetic radiation that optically interacts with a sample to produce sample-interacted light; and a tunable detector configured to: respond to one or more predetermined wavelengths of the sample-interacted light; apply a weight based on an intensity of the response to the one or more wavelengths of the sample-interacted light; and generate a signal utilized for determining a characteristic of the sample.

2. The optical computing device of paragraph 1. further comprising a signal processor communicably coupled to the detector to computationally determine the characteristic of the sample.

3. The optical computing device of any of paragraphs 1-2, wherein the signal processor comprises one or more processors and a memory.

4. The optical computing device of paragraph 1, wherein the tunable detector comprises one or more structures having at least one structure characteristic optimized to respond to and weight the one or more predetermined wavelengths of the sample-interacted light.

5. The optical computing device of any of paragraphs 1-4, wherein the one or more structures comprise non-planar semiconductor structures.

6. The optical computing device of any of paragraphs 1-5, wherein the non-planar semiconductor structures comprise at least one of a fin, a metal ridge, and a base layer.

7. The optical computing device of any of paragraphs 1-4, wherein the at least one structure characteristic comprises a dimension of the one or more structures.

8. The optical computing device of any of paragraphs 1-7, wherein the at least one structure characteristic comprises at least one of a width of a fin, a height of a fin, a pitch between adjacent fins, a thickness of a metal ridge, and a thickness of a base layer.

9. The optical computing device of paragraph 1, wherein the tunable detector comprises a plurality of cells each including one or more structures having at least one structure characteristic optimized to respond to and weight the one or more predetermined wavelengths of the sample-interacted light.

10. The optical computing device of any of paragraphs 1-9, wherein the plurality of cells are individually addressable to respond the one or more predetermined wavelengths of the sample-interacted light the cell is optimized to respond to and weight.

11. The optical computing device of any of paragraphs 1-9, wherein the tunable detector comprises an array of tunable detectors.

12. The optical computing device of paragraph 1, wherein the optical computing device is configured for use in a downhole tool.

13. The optical computing device of paragraph 1, wherein the optical computing device is configured for use in a logging while drilling (LWD) tool.

14. An optical computing method, comprising: irradiating a sample with electromagnetic radiation to produce sample-interacted light; addressing one or more cells of a tunable detector to tune the detector to respond to and weight one or more wavelengths of the sample-interacted light, the one or more wavelengths corresponding to one or more characteristics of the sample; generating a signal from the weighted one or more wavelengths of sample-interacted light incident on the tuned detector; and processing the generated signal to identify the characteristics of the sample.

15. The optical computing method of paragraph 14, wherein addressing the one or more cells of the tunable detector comprises addressing one or more cells comprising one or more structures having structure characteristics optimized to respond to and weight the one or more wavelengths.

16. The optical computing method of paragraph 14, wherein the one or more structures comprise non-planar semiconductor structures and the structure characteristics comprise dimensions of the non-planar semiconductor structures.

17. The optical computing method of paragraph 14, wherein generating the signal comprises generating the signal proportional to the characteristics of the sample.

18. The optical computing method of paragraph 14, wherein the weight corresponds to an intensity of a response to the one or more wavelengths.

The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:

1. An optical computing device, comprising:
an electromagnetic radiation source configured to produce electromagnetic radiation that optically interacts with a sample to produce sample-interacted light; and
a tunable detector configured to:
respond to one or more predetermined wavelengths of the sample-interacted light;
apply a weight based on an intensity of the response to the one or more wavelengths of the sample-interacted light; and
generate a signal utilized for determining a characteristic of the sample,
wherein the tunable detector comprises one or more structures having at least one structure characteristic optimized to respond to and weight the one or more predetermined wavelengths of the sample-interacted light.

2. The optical computing device of claim 1, further comprising a signal processor communicably coupled to the detector to computationally determine the characteristic of the sample.

3. The optical computing device of claim 2, wherein the signal processor comprises one or more processors and a memory.

4. The optical computing device of claim 1, wherein the one or more structures comprise non-planar semiconductor structures.

5. The optical computing device of claim 4, wherein the non-planar semiconductor structures comprise at least one of a fin, a metal ridge, and a base layer.

6. The optical computing device of claim 1, wherein the at least one structure characteristic comprises a dimension of the one or more structures.

7. The optical computing device of claim 6, wherein the at least one structure characteristic comprises at least one of a width of a fin, a height of a fin, a pitch between adjacent fins, a thickness of a metal ridge, and a thickness of a base layer.

8. The optical computing device of claim 1, wherein the tunable detector comprises a plurality of cells each including one or more structures having at least one structure characteristic optimized to respond to and weight the one or more predetermined wavelengths of the sample-interacted light.

9. The optical computing device of claim 8, wherein the plurality of cells are individually addressable to respond the one or more predetermined wavelengths of the sample-interacted light the cell is optimized to respond to and weight.

10. The optical computing device of claim 8, wherein the tunable detector comprises an array of tunable detectors.

11. The optical computing device of claim 1, wherein the optical computing device is configured for use in a downhole tool.

12. The optical computing device of claim 1, wherein the optical computing device is configured for use in a logging while drilling (LWD) tool.

13. An optical computing method, comprising:
    irradiating a sample with electromagnetic radiation to produce sample-interacted light;
    addressing one or more cells of a tunable detector to tune the detector to respond to and weight one or more wavelengths of the sample-interacted light, the one or more wavelengths corresponding to one or more characteristics of the sample;
    generating a signal from the weighted one or more wavelengths of sample-interacted light incident on the tuned detector; and
    processing the generated signal to identify the characteristics of the sample,
    wherein addressing the one or more cells of the tunable detector comprises addressing one or more cells comprising one or more structures having structure characteristics optimized to respond to and weight the one or more wavelengths.

14. The optical computing method of claim 13, wherein the one or more structures comprise non-planar semiconductor structures and the structure characteristics comprise dimensions of the non-planar semiconductor structures.

15. The optical computing method of claim 13, wherein generating the signal comprises generating the signal proportional to the characteristics of the sample.

16. The optical computing method of claim 13, wherein the weight corresponds to an intensity of a response to the one or more wavelengths.

* * * * *